United States Patent [19]

Carroll et al.

[11] Patent Number: 4,972,835
[45] Date of Patent: Nov. 27, 1990

[54] IMPLANTABLE CARDIAC DEFIBRILLATOR EMPLOYING AN IMPROVED SENSING SYSTEM WITH NON-BINARY GAIN CHANGES

[75] Inventors: Kenneth J. Carroll, San Jose; Benjamin D. Pless, Menlo Park, both of Calif.

[73] Assignee: Ventritex, Inc., Sunnyvale, Calif.

[21] Appl. No.: 353,955

[22] Filed: May 19, 1989

[51] Int. Cl.[5] .............................................. A61N 1/00
[52] U.S. Cl. .................................................. 128/419 D
[58] Field of Search .................... 128/419 D, 695, 696, 128/705

[56] References Cited

U.S. PATENT DOCUMENTS

| 3,698,386 | 10/1972 | Fried | 128/705 |
|---|---|---|---|
| 4,184,493 | 1/1980 | Langer et al. | 128/419 D |
| 4,403,614 | 9/1983 | Engle et al. | 128/419 D |
| 4,494,551 | 1/1985 | Little, III et al. | 128/696 |
| 4,521,743 | 6/1985 | Heimer | 330/296 |
| 4,819,643 | 4/1989 | Menken | 128/419 PG |
| 4,830,006 | 5/1989 | Halusk et al. | 128/419 PG |

Primary Examiner—Lee S. Cohen
Assistant Examiner—Scott M. Getzow
Attorney, Agent, or Firm—Gerstman & Ellis, Ltd.

[57] ABSTRACT

An implantable cardiac defibrillator includes electrodes coupled to a patient's heart, a sensing system having inputs connected to the electrodes for sensing cardiac electrical signals from the atrial and/or ventricular channels, means for storing a charge, and means for delivering a shock to the heart. The sensing system includes switched capacitor means for amplifying the cardiac electrical signal with non-binary gain changing steps.

20 Claims, 3 Drawing Sheets

IMPLANTABLE CARDIAC DEFIBRILLATOR EMPLOYING AN IMPROVED SENSING SYSTEM WITH NON-BINARY GAIN CHANGES

BACKGROUND OF THE INVENTION

This invention relates generally to implantable medical devices and more particularly, it relates to an implantable cardiac defibrillator employing an improved sensing system with non-binary gain changes so as to maintain its output in a desired range.

In recent years, there has been substantial progress made in the research and development of defibrillating devices for providing an effective medical response to various disorders, such as ventricular fibrillation. Research efforts have also been made toward developing improved sensing techniques for reliably monitoring heart activity so as to determine when a defibrillating high energy shock is required.

However the implantable cardiac defibrillators of the prior art used comparatively simple sensing circuits. These prior art sensing circuits would typically include switched capacitor circuits. When it was desired to make a gain change, e.g., by switching in an additional capacitor, the output of the prior art switched capacitor circuits would be increased by a factor of two for each increase in binary gain code. In other words, there would be a doubling of the gains for each binary gain code. If it is desired to maintain an output between a desired range such as normally 65% and 90% of full scale, the prior art gain changing method could result in a hunting or oscillating effect above and below the desired range, thereby destroying the integrity of the sensed ECG heart signals.

It would therefore be desirable to provide an implantable cardiac defibrillator employing an improved sensing system for processing ECG heart signals from the atrial and/or ventricular channels where the gains thereof are changed in a non-binary fashion, thereby avoiding hunting.

SUMMARY OF THE INVENTION

Accordingly, it is a general object of the present invention to provide an implantable medical device employing an improved sensing system for processing ECG heart signals from the atrial and/or ventricular channels where the gains thereof are changed in a non-binary fashion, thereby avoiding hunting.

It is another object of the present invention to provide an implantable medical device employing an improved sensing system which includes switched capacitor circuits for amplifying ECG heart signals with non-binary gain changing steps.

It is still another object of the present invention to provide an improved implantable medical device employing an improved sensing means which includes a first switched capacitor amplifier having a first controllable gain and a second switched capacitor amplifier having a second controllable gain.

It is still another object of the present invention to provide an implantable medical device which includes a sensing system formed of a first differential amplifier stage with a fixed gain, a second amplifier/gain stage having a first controllable gain, and a third amplifier/gain stage having a second controllable gain.

In accordance with these aims and objectives, the present invention is concerned with the provision of an implantable medical device which includes electrodes coupled to a patient's heart and a sensing system having its inputs connected to the electrodes for sensing cardiac electrical signals from the artrial and/or ventricular channels. The sensing system includes switched capacitor means for amplifying the cardiac electrical signals with non-binary incremental gain steps.

BRIEF DESCRIPTION OF THE DRAWINGS

These and other objects and advantages of the present invention will become more fully apparent from the following detailed description when read in conjunction with the accompanying drawings with like reference numerals indicating corresponding parts throughout, wherein.

DESCRIPTION OF THE PREFERRED EMBODIMENT

Figure 1:
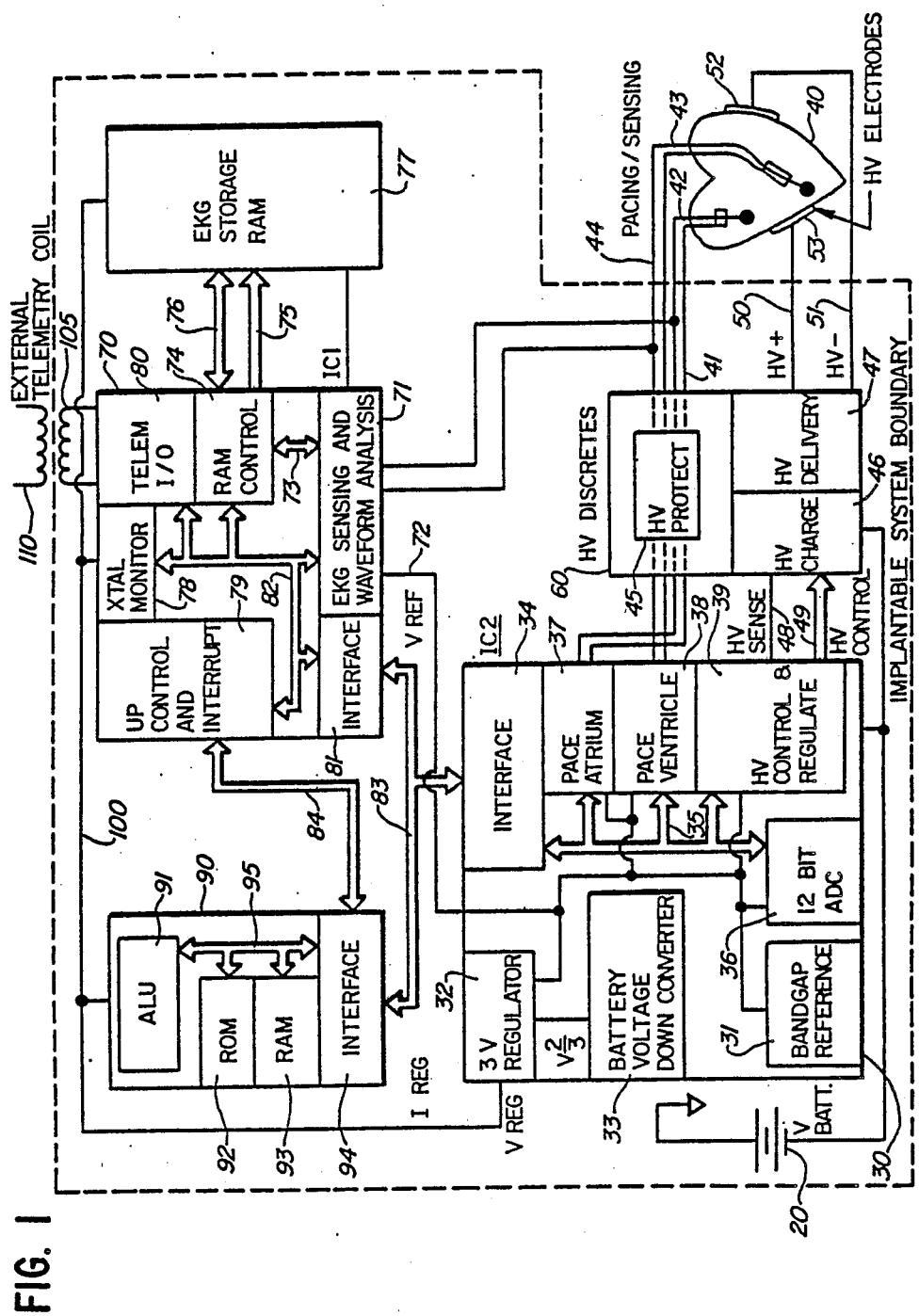
FIG. 1 is a block diagram of an implantable cardiac defibrillator, constructed in accordance with the principles of the present invention.

In FIG. 1, there is illustrated in a functional block diagram format the internal and external elements of an implantable cardiac defibrillator constructed in accordance with the principles of the present invention. A detailed description of the elements of FIG. 1 as well as their interconnection and operation has been presented in co-pending application Ser. No. 344,011, filed Apr. 26, 1989 in the names of Benjamin D. Pless and Phillip L. Ball, entitled "Method For Cardiac Defibrillation" and assigned to the same assignee as the present invention, which is hereby incorporated by reference. Thus, the detailed description will not herein be repeated. However, a general description of the elements of FIG. 1 required for an understanding of the present invention will be presented.

In particular, FIG. 1 shows an implantable cardiac defibrillator which includes four integrated circuit chips IC1-IC4 and a set of high voltage discrete component blocks 45-47. The block 45 contains high voltage protection circuits which prevent the atrium and ventricle pacing circuits 37 and 38 from being damaged by the defibrillation voltage. The block 46 is a high voltage charge block and contains a high voltage capacitor that is charged to deliver a defibrillating pulse. The defibrillating pulse is delivered from the high voltage delivery block 47 to electrodes 52 and 53 connected to the heart 40 via lines 50 and 51.

The chip IC1 contains an ECG sensing and waveform analysis block 71 which receives ECG heart signals to be monitored and processed. Specifically, the heart signals coming from the atrium are fed to the sensing and waveform analysis block 71 via the line 42. The heart signals coming from the ventricle are fed to the block 71 via the line 44.

The block 71 includes a sensing system formed of a first three-stage amplifier/filter network for sensing the analog heart signals in the atrium and a second three-stage filter network for sensing the analog heart signals in the ventricle. The sensing system 10 is illustrated in block diagram form in FIG. 2 for providing outputs which have non-binary gain changing steps.

Figure 2:
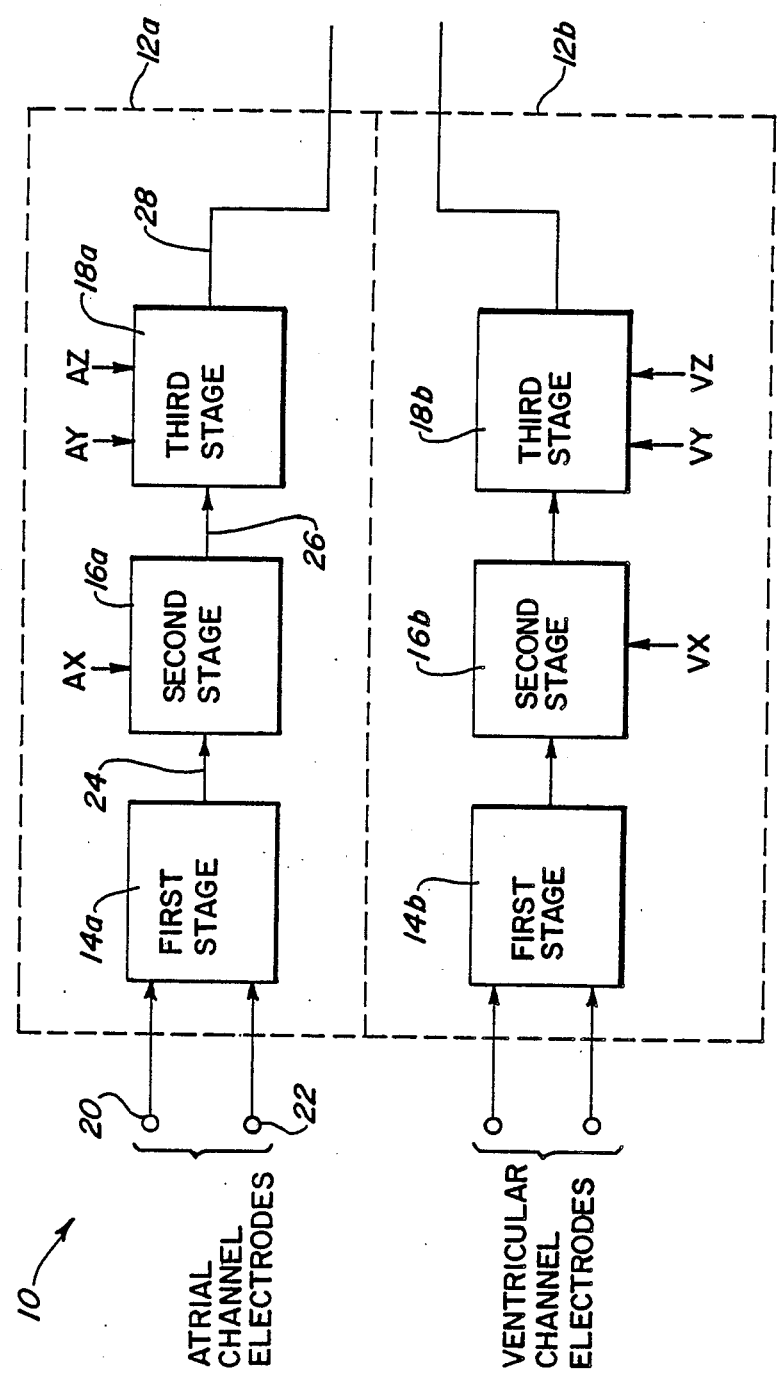
FIG. 2 is a simplified block diagram of a sensing system, constructed in accordance with the principles of the present invention.

Referring now to FIG. 2 of the drawings, there is shown in block diagram form an improved sensing system 10 of the present invention which is formed of a first three-stage amplifier/filter sensing network 12a for sensing the heart signals in the atrium and a second three-stage amplifier/filter sensing network 12b for sensing the heart signals in the ventricle. The first sensing network 12a is comprised of a first stage 14a, a second stage 16a, and a third stage 18a. Similarly, the second sensing network 12b is comprised of a first stage 14b, a second stage 16b, and a third stage 18b. Since the first and second sensing networks are identical in construction, it will be sufficient to discuss in detail only the components of the first sensing network 12a.

The first stage 14a receives ECG heart signals from the atrial channel via a pair of input terminals 20, 22 defining the inputs of the sensing system and provides an output on line 24. The first stage 14a includes a differential amplifier with a fixed gain for eliminating common mode noise problems and an anti-aliasing filter for removing of certain unwanted frequencies in the original ECG heart signals. The second stage 16a includes a first switched capacitor gain amplifier whose input is connected to the output of the first stage on the line 24 and provides an output on line 26 which has a first controllable gain.

The third stage 18a includes a second switched capacitor gain amplifier whose input is connected to the output of the second stage on the line 26 and provides an output on line 28 which has a second controllable gain. The gain settings of the second and third stages are microprocessor controlled by a three-bit binary gain code so as to provide non-binary gain changing steps between the input of the second stage 16a and the output of the third stage 18a, as will be described more fully hereinafter.

Figure 3:
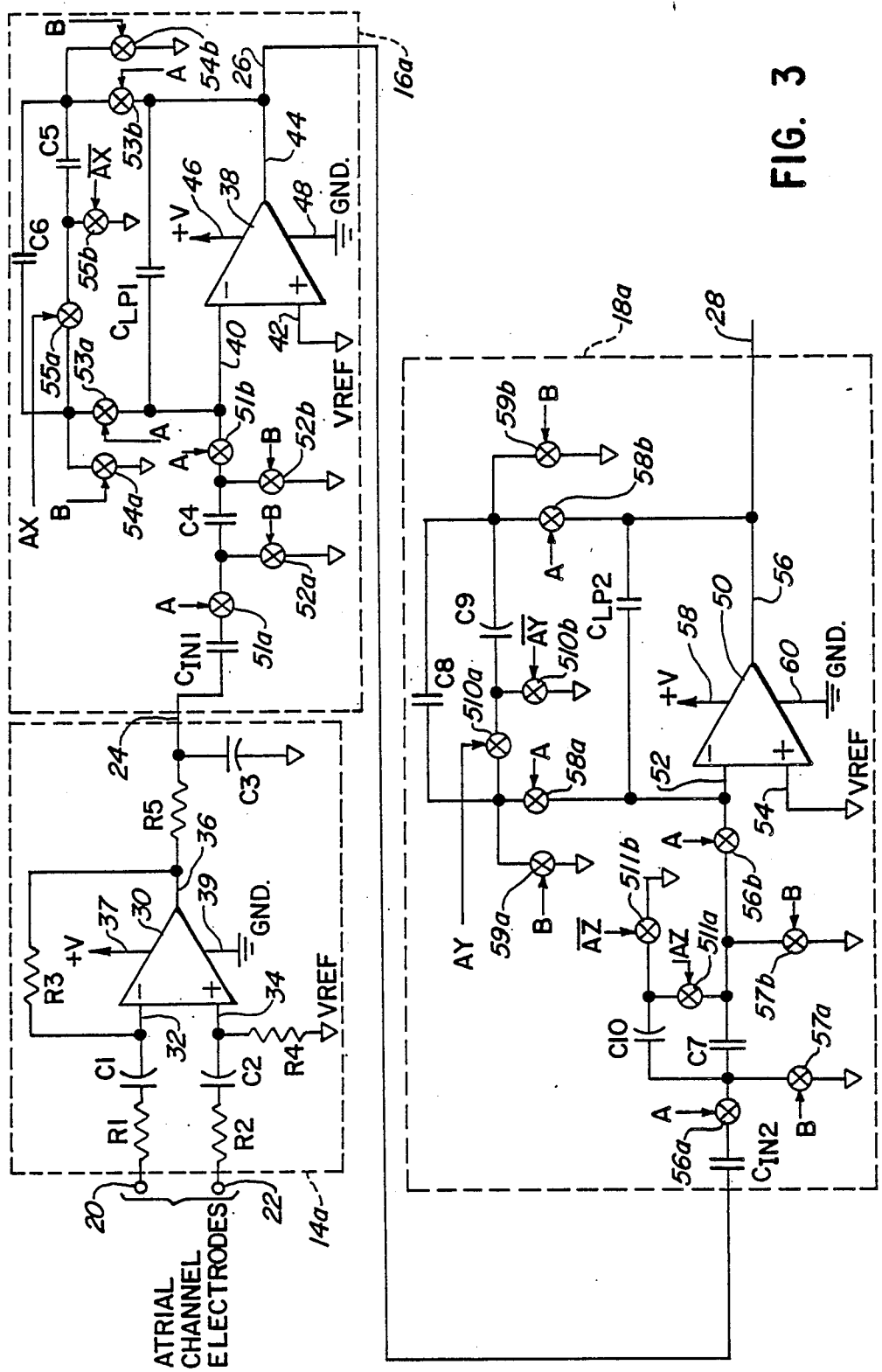
FIG. 3 is a schematic circuit diagram of the atrial channel sensing network of FIG. 2.

In FIG. 3, there is shown a detailed schematic circuit diagram of the first sensing network 12a of FIG. 2. The first stage 14a of the sensing network 12a consists of the differential amplifier formed of an operational amplifier 30 having an inverting input terminal 32, a non-inverting input terminal 34, and an output terminal 36. The operational amplifier has a lead line 37 connected to a supply potential +V and a lead line 39 connected to a battery ground potential GND.

A high pass filter formed of series-connected input resistor R1 and capacitor C1 is coupled between the input terminal 20 and the inverting input terminal 32 of the operational amplifier. A high pass filter formed of a series-connected input resistor R2 and capacitor C2 is coupled between the input terminal 22 and the non-inverting input terminal 34 of the operational amplifier. A feedback resistor R3 is connected between the inverting input terminal 34 and the output terminal 36 of the operational amplifier.

An impedance balancing resistor R4 has its one end connected to the non-inverting input terminal 34 and its other end connected to a reference potential VREF, which is set to a "mid-rail" voltage of +1.235 volts. A series-connected resistor R5 and capacitor C3 is coupled between the output terminal 36 and the reference potential. The junction of the resistor R5 and the capacitor C3 is connected to the line 24 defining the output of the first stage.

The operational amplifier provides a fixed gain determined by the ratio of the feedback resistor R3 and the input resistor R1 and provides a level shifting from the ground potential where the heart is referenced, to the reference potential VREF. The values of the input resistors R1, R2 and the capacitors C1, C2 are selected so as to form the high pass filter with a break frequency of approximately 10 Hz. The values of the resistors R5 and the capacitor C3 are selected so as to form the low pass filter with a break frequency of 60 Hz. This low pass filter defines an anti-aliasing filter for attenuating the unwanted signal frequencies above one-half of the sampling frequency used in the switched capacitor amplifiers of the second and third stages.

The second stage 16a of the sensing network 12a consists of the first switched capacitor gain amplifier formed of an operational amplifier 38 having an inverting input terminal 40, a non-inverting input terminal 42, and an output terminal 44. The operational amplifier 38 has a lead line 46 connected to the supply potential +V and a lead line 48 connected to the ground potential. The output terminal 44 is connected to the line 26 defining the output of the second stage.

The non-inverting input terminal 42 is connected to the reference potential VREF. An input capacitor $C_{in1}$ and a switched capacitor resistor equivalent $R_{eq1}$ consisting of a capacitor C4 and switches S1a, S1b, S2a, S2b are connected between the output of the first stage of the line 24 and the inverting input terminal 40 of the operational amplifier 38. The values of the input capacitor $C_{in1}$ and the resistor equivalent $R_{eq1}$ are selected so as to form a high pass filter with a break frequency of approximately 10 Hz.

A filter capacitor $C_{LP1}$ has its one end connected to the output terminal 44 and its other end connected to the inverting input terminal 40 of the operational amplifier 38. A switched capacitor resistor equivalent $R_{eq2}$ consisting of a capacitor C6 and switches S3a, S3b, S4a, S4b are connected between the output terminal 44 and the inverting input terminal 40 of the operational amplifier. The values of the filter capacitor $C_{LP1}$ and the resistor equivalent $R_{eq2}$ are selected so as to form a low pass filter with a break frequency of 100 Hz. Further, the ratio $R_{eq2}/R_{eq1}$ of the two switched capacitor resistor equivalents are selected so as to provide a gain of twenty. For example, the capacitance value of the capacitor C4 is chosen to be 20C and the capacitance value of the capacitor C6 is chosen to be 1C. Thus, the gain A1 is given by:

$$\text{gain } A1 = \frac{R_{eq2}}{R_{eq1}}, \quad (1)$$

where $$R_{eq2} = 1/C6 \quad (2)$$

and $$R_{eq1} = 1/C4 \quad (3)$$

By substituting equations (2) and (3) into equation (1) and inserting the capacitance values, the gain A1 is found to be:

$$\text{gain } A1 = \frac{1/C6}{1/C4} = \frac{C4}{C6} = \frac{20C}{1C} = 20 \quad (4)$$

In order to change the gain A1, there is provided a series-connection of an additional capacitor C5, which is chosen to have a capacitance value of 4C, and gain-select switches S5a and S5b for selectively coupling the capacitor C5 to be in parallel with the capacitor C6. When the switch S5a is closed by a gain control signal AX generated by the microprocessor, the capacitors C6 and C5 are connected together in parallel. Therefore a new gain A2 will be equal to $C4/(C6+C5)$ or $20C/5C=4$. Accordingly, the second stage 16a has been designed to provide the controllable gain of either $A1=20$ or $A2=4$.

The third stage 18a of the sensing network 12a consists of the second switched capacitor gain amplifier formed of an operational amplifier 50 having an inverting input 52, a non-inverting input 54 and an output terminal 56. The operational amplifier has a lead line 58 connected to the supply potential $+V$ and a lead line 60 connected to the ground potential. The output terminal 56 is connected to the ground line 28 defining the output of the third stage as well as the output of the sensing system 10.

The non-inverting input terminal 54 is connected to the reference potential VREF. An input capacitor $C_{in2}$ and a switched capacitor resistor equivalent $R_{eq3}$ consisting of a capacitor C7 and switches S6a, S6b, S7a, S7b are connected between the output of the second stage on the line 26 and the inverting input terminal 52 of the operational amplifier 50. The values of the input capacitor $C_{in2}$ and the resistor equivalent $R_{eq3}$ are selected so as to form a high pass filter with a break frequency of approximately 1.5 Hz.

A filter capacitor $C_{LP2}$ has its one end connected to the output terminal 56 and its other end connected to the inverting input terminal 52 of the operational amplifier 50. A switched capacitor resistor equivalent $R_{eq4}$ consisting of a capacitor C8 and switches S8a, S8b, S9a, S9b are connected between the output terminal 56 and the inverting input terminal 52 of the operational amplifier. The gain A3 is equal to the ratio of C7/C8. If the capacitance value of the capacitor C8 is chosen to be 2C and the capacitance value of the capacitor C7 is chosen to be 5.3C, then the gain A3 will be equal to $5.3C/2C=2.65$.

In order to change the gain A3, there is provided a parallel-connection of an additional capacitor C9, which is chosen to have a capacitance value of 1C, and gain-select switches S10a and S10b. The capacitor C9 is selectively coupled in parallel with the capacitor C8. When the switch S10a is closed in response to a gain control signal AY generated by the microprocessor, the capacitors C8 and C9 are connected together in parallel. Therefore, a new gain A4 will be equal to $C7/(C8+C9)$ or $5.3C/3C=1.77$.

Further, there is also provided a parallel connection of an additional capacitor C10, which is chosen to have a capacitance value of 6.8C, and gain-select switches S11a and S11b. The capacitor C10 is selectively coupled in parallel with the capacitor C7. With the gain-select switch S10a opened and the gain-select switch S11a closed in response to a gain control signal AZ generated by the microprocessor, the capacitors C7 and C10 are connected in parallel. Therefore, a new gain A5 will be equal to $(C7+C10)/C8$ or $12.1C/2C=6.05$.

On the other hand, if both the gain-select switches S10a and S11a are closed due to the respective control signals AY and AZ, the capacitors C8 and C9 will be connected together in parallel and the capacitors C7 and C10 will be connected in parallel. As a result, a new gain A6 will be equal to $(C7+C10)/(C8+C9)$ or $12.1C/3C=4.03$. Accordingly, it can be seen that the third stage has been designed to provide the controllable gain setting of either $A3=2.65$, $A4=1.77$, $A5=6.05$, or $A6=4.03$.

Listed below is a table arranged in four columns showing the possible gain settings of the second stage, the possible gain settings of the third stage, the overall gain setting of the second and third stages, and the corresponding gain changing steps. It will be noted that the overall gain setting is obtained by multiplying the gain A1 of the second stage with each of the possible gain settings of the third stage and by multiplying the gain A2 of the second stage with each possible gain setting of the third stage. After rearranging the overall gain settings in ascending order, the values in the third column are realized. Thus, it will be understood that each of the gain changing steps shown in the fourth column (differences between adjacent gain settings in the third column) is non-binary and is increased approximately 1.5 each time.

TABLE

| Second Stage Gain | Third Stage Gain | Overall Gain | Gain Changing Steps |
|---|---|---|---|
| A1 = 20 | A3 = 2.65 | 7.08 | |
| A2 = 4 | A4 = 1.77 | 10.6 | 1.49 |
| | A5 = 6.05 | 16.12 | 1.6 |
| | A6 = 4.03 | 24.2 | 1.5 |
| | | 35.4 | 1.46 |
| | | 53 | 1.50 |
| | | 81 | 1.53 |
| | | 121 | 1.49 |

From the foregoing detailed description, it can thus be seen that the present invention provides an implantable cardiac defibrillator which employs an improved sensing system for processing ECG heart signals from the atrial and/or ventricular channels where the gains thereof are changed in a non-binary fashion, thereby avoiding the potential of hunting. The sensing system includes a first switched capacitor amplifier having a first controllable gain and a second switched capacitor amplifier having a second controllable gain.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

What is claimed is:

1. An implantable medical device comprising:
   electrode means for coupling to a patient's heart;
   sensing means having inputs connected to said electrode means for sensing cardiac electrical signals from the heart; and
   said sensing means including amplifying means, said amplifying means including switched capacitor means for amplifying said cardiac electrical signals with non-binary gain changing steps.

2. An implantable medical device as claimed in claim 1, wherein said switched capacitor means is formed of a first switched capacitor amplifier having a first controllable gain and a second switched capacitor amplifier having a second controllable gain.

3. An implantable medical device as claimed in claim 2, wherein said first controllable gain is determined by a ratio of plural capacitors connected to said first switched capacitor amplifier.

4. An implantable medical device as claimed in claim 3, wherein said second controllable gain is determined by ratios of plural capacitors connected to said second switched capacitor amplifier.

5. An implantable medical device as claimed in claim 4, wherein the combined gains of said first and second controllable gains provides the non-binary gain changing steps in steps of approximately 1.5.

6. An implantable medical device as claimed in claim 1, wherein said sensing means further includes a differential amplifier means having its inputs coupled to input terminals to receive said cardiac electrical signals for generating on its output a first output signal to be received by said switched capacitor means.

7. An implantable medical device as claimed in claim 6, further comprising high pass filter means coupled between said input terminals and said inputs of said differential amplifier means.

8. An implantable medical device as claimed in claim 7, further comprising low pass filter means defining an anti-aliasing filter coupled to the output of said differential amplifier means.

9. An implantable medical device as claimed in claim 8, wherein said high pass filter means has a break frequency of approximately 10 Hz and said low pass filter means has a break frequency of approximately 60 Hz.

10. An implantable medical device comprising:
electrode means for coupling to a patient's heart;
sensing means having inputs connected to said electrode means for sensing cardiac electrical signals from the atrial and/or ventricular channels;
means for storing a charge;
means coupled to said storing means for delivering a shock to the heart; and
said sensing means including differential amplifier means having its inputs coupled to input terminals to receive said cardiac electrical signals and switched capacitor means responsive to said differential amplifier means for amplifying said cardiac electrical signals with non-binary gain changing steps, said switched capacitor means being formed of a first switched capacitor amplifier having a first controllable gain and a second switched capacitor amplifier having a second controllable gain.

11. An implantable medical device as claimed in claim 10, wherein said first controllable gain is determined by a ratio of plural capacitors connected to said first switched capacitor amplifier.

12. An implantable medical device as claimed in claim 11, wherein said second controllable gain is determined by ratios of plural capacitors connected to said second switched capacitor amplifier.

13. An implantable medical device as claimed in claim 12, wherein the combined gains of said first and second controllable gains provides the non-binary gain changing steps in steps of approximately 1.5 each time.

14. An implantable medical device as claimed in claim 13, further comprising high pass filter means coupled between said input terminals and said inputs of said differential amplifier means.

15. An implantable medical device as claimed in claim 14, further comprising low pass filter means defining an anti-aliasing filter coupled to an output of said differential amplifier means.

16. An implantable medical device as claimed in claim 15, wherein said high pass filter means has a break frequency of approximately 10 Hz and said low pass filter means has a break frequency of approximately 60 Hz.

17. An implantable medical device comprising:
electrode means for coupling to a patient's heart;
sensing means having inputs connected to said electrode means for sensing cardiac electrical signals from the atrial and/or ventricular channels;
means for storing a charge;
means coupled to said storing means for delivering a shock to the heart; and
said sensing means including means for amplifying said cardiac electrical signals with non-binary gain changing steps, said amplifying means including a first amplifier/gain stage formed of a differential amplifier with a fixed gain, a second amplifier/gain stage formed of a first switched capacitor amplifier having a first controllable gain, and a third amplifier/gain stage formed of a second switched capacitor amplifier having a second controllable gain.

18. An implantable medical device as claimed in claim 17, wherein said first controllable gain is determined by a ratio of plural capacitors connected to said first switched capacitor amplifier.

19. An implantable medical device as claimed in claim 18, wherein said second controllable gain is determined by ratios of plural capacitors connected to said second switched capacitor amplifier.

20. An implantable medical device as claimed in claim 19, further comprising low pass filter means defining an anti-aliasing filter coupled to an output of said differential amplifier.

* * * * *